(12) United States Patent
Russo

(10) Patent No.: US 11,864,924 B2
(45) Date of Patent: Jan. 9, 2024

(54) METHODS AND APPARATUS FOR TIME-VARYING FILTERING OF SIGNALS OF CONTINUOUS ANALYTE MONITORING SYSTEMS

(71) Applicant: Ascensia Diabetes Care Holdings AG, Basel (CH)

(72) Inventor: Anthony P. Russo, New York, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 121 days.

(21) Appl. No.: 17/337,133

(22) Filed: Jun. 2, 2021

(65) Prior Publication Data

US 2021/0378598 A1 Dec. 9, 2021

Related U.S. Application Data

(60) Provisional application No. 63/112,138, filed on Nov. 10, 2020, provisional application No. 63/034,971, filed on Jun. 4, 2020.

(51) Int. Cl.
| | |
|---|---|
| *A61B 5/00* | (2006.01) |
| *G16H 40/63* | (2018.01) |
| *A61B 5/145* | (2006.01) |
| *A61B 5/1486* | (2006.01) |

(52) U.S. Cl.
CPC ............ *A61B 5/725* (2013.01); *A61B 5/1451* (2013.01); *A61B 5/14532* (2013.01); *A61B 5/14865* (2013.01); *A61B 5/6849* (2013.01); *A61B 5/7275* (2013.01); *G16H 40/63* (2018.01)

(58) Field of Classification Search
CPC ... A61B 5/725; A61B 5/1451; A61B 5/14532; A61B 5/7275; A61B 5/14865; A61B 5/6849; A61B 5/1455; A61B 5/6833; A61B 5/7225; G16H 40/63
See application file for complete search history.

(56) References Cited

U.S. PATENT DOCUMENTS

| | | | |
|---|---|---|---|
| 2010/0168538 A1* | 7/2010 | Keenan | A61B 5/14532 702/19 |
| 2017/0311897 A1* | 11/2017 | Faccioli | A61B 5/7203 |
| 2019/0150803 A1* | 5/2019 | Vanslyke | A61B 5/7275 |
| 2020/0170508 A1* | 6/2020 | Garcia | A61B 5/743 |

OTHER PUBLICATIONS

Okoniewski, Piotr, and Jacek Piskorowski. "A concept of IIR filters with time-varying coefficients and equalised group delay response." Measurement 60 (2015): 13-24. (Year: 2015).*
U.S. Appl. No. 17/338,247, filed Jun. 2, 2021, Russo.

(Continued)

*Primary Examiner* — Nathan J Jenness
*Assistant Examiner* — Meghan R Kumar
(74) *Attorney, Agent, or Firm* — Erise IP, P.A.

(57) ABSTRACT

A method of filtering a signal in a continuous analyte monitoring (CAM) system includes applying time-varying filtering to the signal using a time-varying filter to generate a filtered continuous analyte monitoring signal during an analyte monitoring period. Other methods, apparatus, continuous analyte monitoring devices, and continuous glucose monitoring devices are also disclosed.

30 Claims, 10 Drawing Sheets

(56) References Cited

OTHER PUBLICATIONS

Chen, Y.Q. et al.: "A new IIR-type digital fractional order differentiator", Signal Processing, Elsevier Science Publishers B.V. Amsterdam, NL, vol. 83, No. 11, Nov. 1, 2003 (Nov. 1, 2003), pp. 2359-2365, XP004463297, ISSN: 0165-1684, DOI: 10-1016/S0165-1684(03)00188-9, p. 2361, equation (4).
Okoniewski, P. et al.: "A concept of IIR filters with time-varying coefficients and equalised group delay response", MEASUREMENT., vol. 60, Jan. 1, 2015 (Jan. 1, 2015), pp. 13-24, XP055841596, GB; ISSN: 0263-2241, D01: 10.1016/j.measurement. 2014.09.077; the whole document.
International Search Report of International Application No. PCT/EP2021/064783 dated Oct. 1, 2021.
European Patent Application 21733065.3, Communication pursuant to Rules 161(1) and 162 EPC, dated Jan. 12, 2023.

\* cited by examiner

METHODS AND APPARATUS FOR TIME-VARYING FILTERING OF SIGNALS OF CONTINUOUS ANALYTE MONITORING SYSTEMS

CROSS REFERENCE TO RELATED APPLICATIONS

This claims the benefit of U.S. Provisional Patent Applications Nos. 63/034,971, filed Jun. 4, 2020, and 63/112,138, filed Nov. 10, 2020, the disclosures of which are hereby incorporated by reference herein in their entireties for all purposes.

FIELD

The present disclosure relates to apparatus and methods for continuous analyte monitoring.

BACKGROUND

Continuous analyte monitoring (CAM), such as continuous glucose monitoring (CGM), has become a routine monitoring operation, particularly for individuals with diabetes. CAM can provide real-time analyte analysis (e.g., analyte concentrations) of an individual. In the case of CGM, real-time glucose concentrations of an individual can be provided. By providing real-time glucose concentrations, therapeutic and/or clinical actions may be applied in a timely fashion to the individual being monitored and a glycemic condition may be better controlled.

Improved CAM and CGM methods and apparatus are therefore desired.

SUMMARY

In some embodiments, a method of filtering a signal in a continuous analyte monitoring system is provided. The method includes applying time-varying filtering to a signal using a time-varying filter to generate a filtered continuous analyte monitoring signal during an analyte monitoring period.

In other embodiments, a method of filtering a continuous glucose monitoring (CGM) signal is provided. The method includes generating a CGM signal, and applying time-varying filtering to the CGM signal using a time-varying filter to generate a filtered continuous analyte monitoring signal during an analyte monitoring period.

In other embodiments, a continuous analyte monitoring (CAM) system is provided. The system includes at least one device configured to generate a signal, and a time-varying filter configured to apply time-varying filtering to the signal during an analyte monitoring period.

Other features, aspects, and advantages of embodiments in accordance with the present disclosure will become more fully apparent from the following detailed description, the claims, and the accompanying drawings by illustrating a number of example embodiments and implementations. Various embodiments in accordance with the present disclosure may also be capable of other and different applications, and its several details may be modified in various respects, all without departing from the scope of the claims and their equivalents. Accordingly, the drawings and descriptions are to be regarded as illustrative in nature, and not as restrictive.

BRIEF DESCRIPTION OF THE DRAWINGS

The drawings, described below, are for illustrative purposes only and are not necessarily drawn to scale. The drawings are not intended to limit the scope of the disclosure in any way. Like numerals are used throughout to denote the same or like elements.

DETAILED DESCRIPTION

Figure 1:
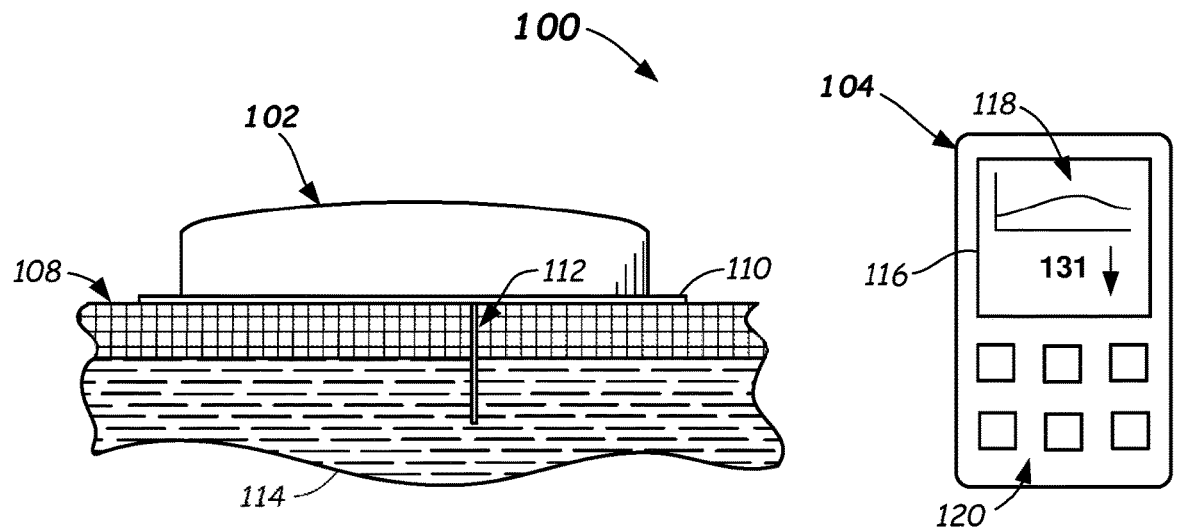
FIG. 1 illustrates a partially cross-sectioned side view and a front elevation view, respectively, of a wearable device and an external device of a continuous analyte monitoring (CAM) system according to embodiments of the disclosure.

A continuous analyte monitoring (CAM) system can measure analyte concentrations in an individual over time and report those analyte concentrations. Some CAM systems include one or more implanted biosensors that directly or indirectly sense (e.g., measure) an analyte present in a bodily fluid and generate one or more signals (e.g., sensor signals or biosensor signals) in response to the sensing. The one or more sensor signals are then processed to generate and/or calculate continuous analyte signals indicative of analyte concentrations over time. The continuous analyte signals are sometimes referred to as "CAM signals" and are reported to a user or a medical provider by way of a display, download, or other communication type.

In some embodiments, the one or more biosensors may comprise one or more probes or the like that pierce the user's skin and are located or implanted subcutaneously into interstitial fluid, for example. In other embodiments, the one or more biosensors may be optical devices that can measure subcutaneous reflectance, for example. The CAM systems may use other types of biosensors.

CAM systems that include a subcutaneous biosensor may monitor current flow between two or more electrodes on the biosensor when the biosensor is located in interstitial fluid. This current flow may be used to determine an analyte concentration (e.g., glucose concentration) in the interstitial fluid. In some embodiments, the biosensor may be contained within and inserted by a trocar (e.g., needle) configured to extend into the user's skin for subcutaneous placement of the biosensor so as to contact interstitial fluid of a user. Upon insertion, the trocar may be removed, leaving behind the implanted biosensor. The biosensor may include electrodes, such as a working electrode, a counter electrode, and/or a reference electrode, for example, that contact the user's interstitial fluid.

During continuous analyte monitoring, a voltage is applied between the electrodes, such as between the working electrode and the counter electrode, and current flow through one or more electrodes is measured. The current flow is proportional to the analyte (e.g., glucose) concentration present in the interstitial fluid. The current flow through the electrodes and the interstitial fluid may be very small, such as a few nanoamperes, which makes the CAM systems very sensitive to noise. When signals indicative of the current flow or other signals within CAM systems are subjected to noise, even a weak noise level, the resulting signal-to-noise ratio may be very low, which results in signals that are difficult to process and/or interpret. In some embodiments, the noise may cause the resulting CAM signal to be jittery, which can make the resulting CAM signal difficult to accurately interpret.

One noise source in CAM systems is caused by degradation of components within the CAM systems, such as over an analyte monitoring period. An analyte monitoring period is the time period over which a biosensor of a CAM system senses analytes. In the example of a biosensor configured to be located subcutaneously, the analyte monitoring period is the time in which the biosensor is located subcutaneously and is actively sensing. An analyte monitoring period may be 14 days or more, for example, i.e., the elapsed length of time during which the biosensor is implanted, sensing, and communicating. In one example, the biosensor properties may degrade as a function of time, which may cause signals generated by the biosensor to become increasingly noisy over the analyte monitoring period. For example, in embodiments wherein the biosensors are located in interstitial fluid, chemicals (e.g., enzymes) deposited on the biosensors that react with the interstitial fluid may degrade and/or deplete during the analyte monitoring period. In some situations, biofilms may also accumulate on the biosensors during the analyte monitoring period.

The degradation and/or depletion of the chemicals may increase or otherwise change during the analyte monitoring period, which causes the sensor signals to be increasingly noisy and/or jittery as the analyte monitoring period progresses. The same may occur with increasing accumulations of biofilms. The noise may be processed with the sensor signals, which yields noisy and/or jittery CAM results that are difficult to interpret or may cause a user to believe that the CAM system is not working correctly.

Apparatus and methods disclosed herein reduce the effects of noise in such CAM systems by applying time-varying filtering to one or more signals in the CAM systems to generate at least one time-varying filtered continuous analyte signal. Noise reduction may be achieved, for example, by smoothing one or more signals generated in the CAM systems using time-varying filtering. The degradation of the biosensors described above and/or degradation of other components over the analyte monitoring period may be known or estimated, which enables the amount of filtering applied by the time-varying filters to be changed (e.g., increased) over the analyte monitoring period in order to filter changing (e.g., increasing) noise levels.

The time-varying filtering described herein may be applied to different signals within the CAM system including, e.g., working electrode current signals, background current signals, CAM signals, estimated device sensitivity signals, and estimated analyte (e.g., glucose) concentration signals. The time-varying filtering smooths the signals and/or reduces the effects of noise and/or algorithm artifacts, which improves a user's ability to interpret the analyte concentrations. The time-varying filtering may be applied as a function of the amount of time the CAM system has been operational. For example, the filtering may be changed by adjusting the smoothing parameters accordingly so as to respond to changes (e.g., sensor degradation) over time.

These and other apparatus and methods are described in detail with reference to FIGS. 1-8. Embodiments of time-varying filtering apparatus and methods are described herein with reference to continuous glucose monitoring (CGM) systems. However, the time-varying filtering apparatus and methods described herein may be applied to other continuous analyte monitoring (CAM) systems that measure analytes, such as cholesterol, lactate, uric acid, and alcohol, for example.

Reference is now made to FIG. 1, which illustrates an example of a continuous glucose monitoring (CGM) system 100 including a wearable device 102 and an external device 104. As described herein, the wearable device 102 measures glucose concentrations and the external device 104 displays the glucose concentrations. In some embodiments, the wearable device 102 may also display glucose concentrations. The wearable device 102 may be attached (e.g., adhered) to the skin 108 of a user such as by an adhesive-backed layer 110, for example.

The wearable device 102 may include a biosensor 112 that may be located subcutaneously in interstitial fluid 114 of a user and may directly or indirectly measure glucose concentrations. The wearable device 102 may transmit the glucose concentrations to the external device 104, where the glucose concentrations may be displayed on an external display 116. The external display 116 may display different formats of glucose concentrations, such as individual numbers, graphs, and/or tables. In the example embodiment of FIG. 1, the external display 116 is displaying a graph 118 showing past and present glucose concentrations and a number indicating a glucose concentration from a most recent glucose calculation. The external display 116 may also display glucose trends as noted by the downward arrow 131 shown on the external display 116, indicating that the user's blood glucose level is currently falling. The external display 116 may display different or additional data in other formats. In some embodiments, the external device 104 may include a plurality of buttons 120 or other input devices that enable users to select data and/or data formats displayed on the external display 116.

Figure 2A:
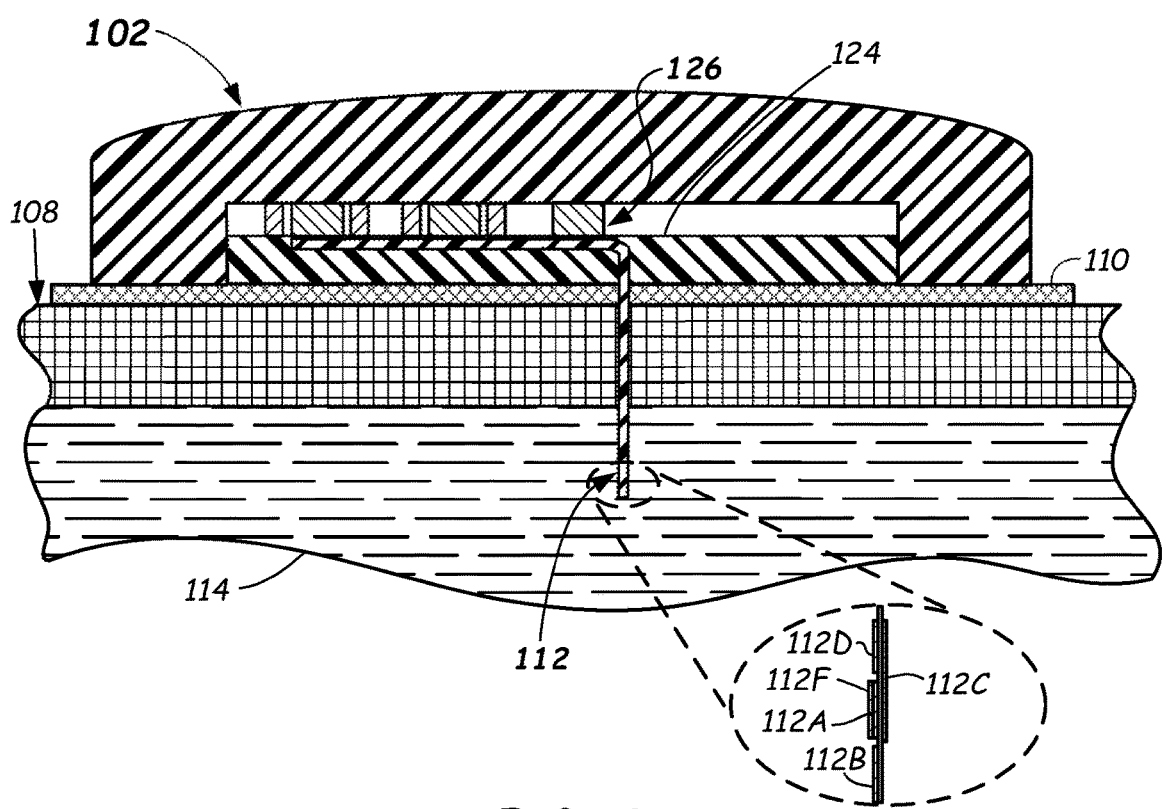
FIG. 2A illustrates a cross-sectioned side view of a wearable device of a CAM system attached to a skin surface according to embodiments of the disclosure.

Reference is now made to FIG. 2A, which illustrates a partial, cross-sectioned side view of the wearable device 102 attached to the skin 108 of a user. The biosensor 112 may be located in interstitial fluid 114 beneath the skin 108 of a user. In the embodiment of FIG. 2A, the biosensor 112 may include a working electrode 112A, a reference electrode 112B, and a counter electrode 112C that may each contact the interstitial fluid 114 as described further below. In some embodiments, the biosensor 112 may include fewer or more electrodes and other electrode configurations. For example, in some embodiments, a second working electrode (e.g., a background electrode) may be employed. The electrodes 112A, 112B, and 112C may be made with and/or coated with one or more chemicals, such as one or more enzymes that react with specific chemical analytes within the interstitial fluid 114. The reactions may change current flow through one or more of the electrodes 112A, 112B, and 112C, which is detected by the wearable device 102 and is used to calculate glucose concentrations as described herein.

Figure 2B:
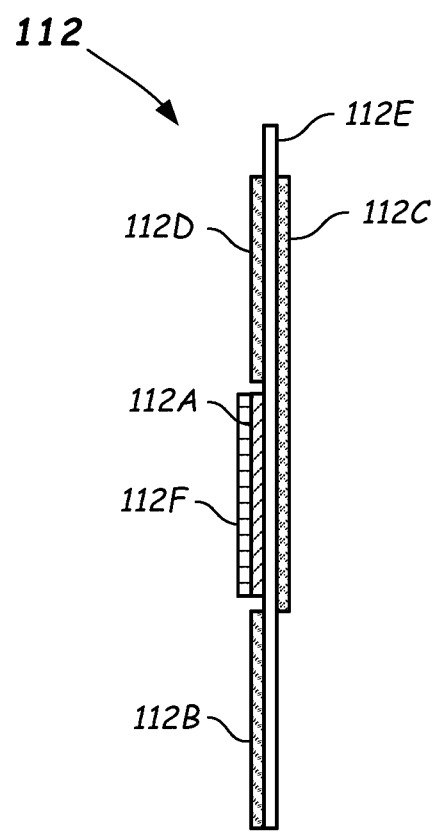
FIG. 2B illustrates a partially cross-sectioned side elevation view of a portion of a biosensor of a CAM system according to embodiments of the disclosure.

FIG. 2B illustrates a cross-sectioned side schematic enlarged partial view of an embodiment of the biosensor 112 in accordance with embodiments provided herein. In some embodiments, the biosensor 112 may include a working electrode 112A, a counter electrode 112C, and a background electrode 112D. The working electrode 112A may include a conductive layer coated with a chemical 112F, which reacts with a glucose-containing solution in a reduction-oxidation reaction, which affects the concentration of charge carriers and time-dependent impedance of the biosensor 112. In some embodiments, the working electrode 112A may be formed from platinum or surface roughened platinum. Other working electrode materials may be used. Example chemical catalysts (e.g., enzymes) for the working electrode 112A include glucose oxidase, glucose dehydrogenase, or the like. The enzyme component may be immobilized onto the electrode surface by a cross-linking agent such as glutaraldehyde, for example. An outer membrane layer (not shown) may be applied onto the enzyme layer to protect the overall inner components including the electrode and the enzyme layer. In some embodiments, a mediator such as ferricyanide or ferrocene may be employed. Other chemical catalysts and/or mediators may be employed.

In some embodiments, the reference electrode 112B may be formed from Ag/AgCl. The counter electrode 112C and/or the background electrode 112D may be formed from a suitable conductor such as platinum, gold, palladium, or the like. Other suitably conductive materials may be used for the reference electrode 112B, the counter electrode 112C, and/or the background electrode 112D. In some embodiments, the background electrode 112D may be identical to the working electrode 112A, but without the chemical catalyst and mediator. The counter electrode 112C may be isolated from the other electrodes by an isolation layer 112E (e.g., polyimide or another suitable material).

The biosensor 112 may include other items and materials that are not shown. For example, the biosensor 112 may include other insulators and the like that electrically insulate the electrodes from one another. The biosensor 112 may also include conductors and the like that electrically couple the electrodes to components in the wearable device 102.

The above-described chemicals on or in the working electrode 112A, the reference electrode 112B, the counter electrode 112C, and the background electrode 112D may become depleted and/or contaminated during an analyte (e.g., glucose) monitoring period. The depletion and/or contamination may cause signals generated by or in conjunction with the biosensor 112 to be noisy and/or jittery as a function of time as described herein. In addition, biofilms may accumulate on the electrodes 112A, 112B, 112C, and/or 112D, which may cause signals generated by the biosensor 112 to become noisier. The time-varying filtering described herein filters or smooths one or more signals within the CGM system 100 to counter effects of the noisy and/or jittery signals.

Returning to FIG. 2A, the wearable device 102 may include a substrate 124 (e.g., a circuit board) on which components 126 of the wearable device 102 may be located. Portions of the substrate 124 may be made of non-conductive materials such as plastic or ceramic. In some embodiments, the substrate 124 may include a laminated material. The substrate 124 may include electrical traces (not shown) that conduct current to components within or attached to the substrate 124, such as the biosensor 112. For example, conductors (not shown) may electrically couple the electrodes 112A, 112B, and 112C to the components 126.

The components 126 may apply a bias voltage across two or more of the electrodes 112A, 112B, 112C, 112D located in the interstitial fluid 114, which results in a bias sensor current flowing through the biosensor 112. Some of the components 126 may be part of circuitry that may measure the sensor current and generate a measured current signal $I_{MEAS}$. In some embodiments, chemicals (enzymes, etc.) on or within the electrodes 112A, 112B, and 112C change impedance in response to contact with glucose or other chemicals or analytes present in the interstitial fluid 114. Thus, the resulting measured current signal $I_{MEAS}$ may be proportional to one or more analytes (e.g., glucose) present in the interstitial fluid 114. During the glucose monitoring period, the chemicals on the electrodes 112A, 112B, and 112C may deteriorate and/or deplete, which may cause the sensor current and the measured current signal $I_{MEAS}$ to become noisy (e.g., jittery) as described above.

The rate at which the chemicals on the electrodes 112A, 112B, 112C, and 112D deteriorate and/or deplete and the rate at which biofilms accumulate on the electrodes 112A, 112B, 112C, and 112D may be known (e.g., experimentally) or otherwise estimated. As described herein, time-varying filtering may be applied to the measured current signal $I_{MEAS}$ and/or other signals in the wearable device 102 and/or the external device 104 to reduce the effects of changes in noise over time. In some embodiments, time-varying filtering may be applied to the resulting CGM signal to reduce noise (e.g., jitter) on the CGM signal. As described herein, the time-varying filtering may change (e.g., increase) attenuation in stop-bands and/or change (e.g., increase) the order of time-varying filtering as a function of time.

Figure 3A:
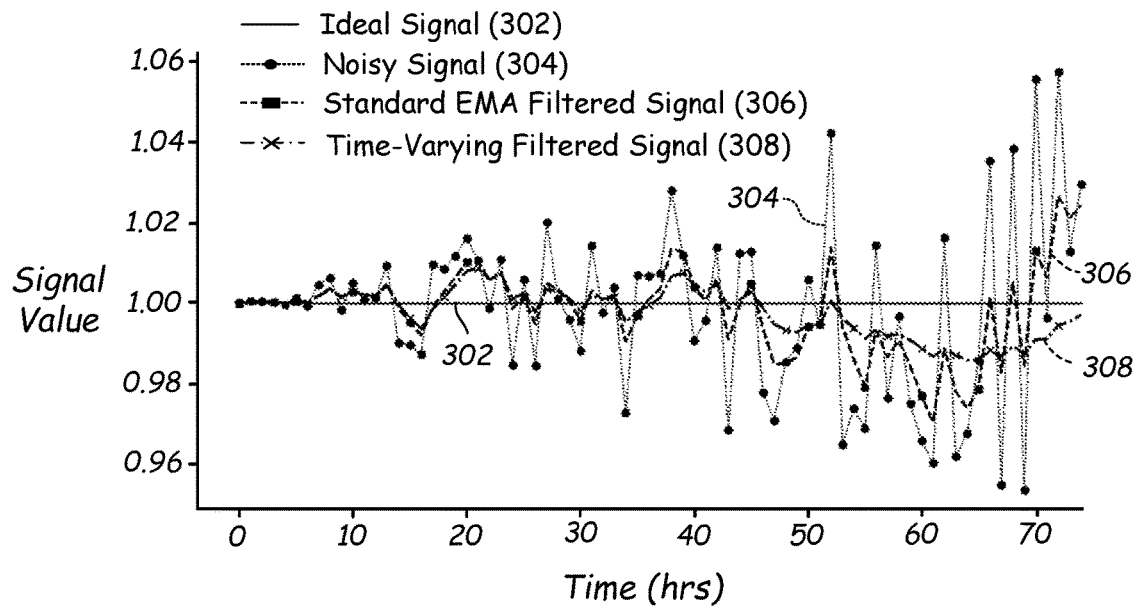
FIG. 3A is a graph illustrating a signal within a CAM system, the signal with noise (noisy signal), the noisy signal with standard filtering applied, and the noisy signal with time-varying filtering applied to according to embodiments of the disclosure.

Reference is now made to FIG. 3A, which is a graph illustrating examples of different filtering effects, including time-varying filtering, on a noisy signal. In the example of FIG. 3A, an ideal signal 302 (solid line) is normalized to a signal value of 1.00. A noisy signal 304, which is the ideal signal 302 with noise added, is shown as a fine-dotted line with dots representing data points thereon. As shown in the example of FIG. 3A, the magnitude of the noisy signal 304 increases as a function of time. A standard exponential moving average (EMA) filtered signal 306, which is the noisy signal 304 after being subjected to standard (EMA) filtering, is shown as a dashed line with squares located therein. The standard EMA filtering is not time dependent and, thus, the filtering applied by the standard EMA filtering does not vary as a function of time. As shown in FIG. 3A, noise on the standard EMA filtered signal 306 continues to increase as a function of time.

When such conventional filtering is applied to signals in a CGM system, the noise on the signals will continue to increase as a function of time. Accordingly, the signal-to-noise ratio of these signals decreases as a function of time, which may render data provided by the CGM system 100 (FIG. 1) inaccurate or difficult to interpret.

A time-varying filtered signal 308 is the result of the noisy signal 304 subjected to time-varying filtering (e.g., time-varying EMA filtering) and is shown in FIG. 3A as a dashed line with x's located thereon. The time-varying filtering that produced the time-varying filtered signal 308 shown in FIG. 3A increases as a function of time. For example, smoothing or high-frequency attenuation may increase as a function of time. Thus, as the magnitude of noise on the ideal signal 302 increases as a function of time as shown by the magnitude of the noisy signal 304 increasing over time, the resulting time-varying filtered signal 308 is more heavily smoothed or filtered as time increases. Accordingly, the resulting time-varying filtered signal 308 that had time-varying filtering applied thereto more closely follows the ideal signal 302. When applied to a CGM system, the time-varying filtering reduces noise that increases during an analyte (e.g., glucose) monitoring period, which enables the user of a CGM system to receive more accurate information regarding analyte (e.g., glucose) concentrations.

Figure 3B:
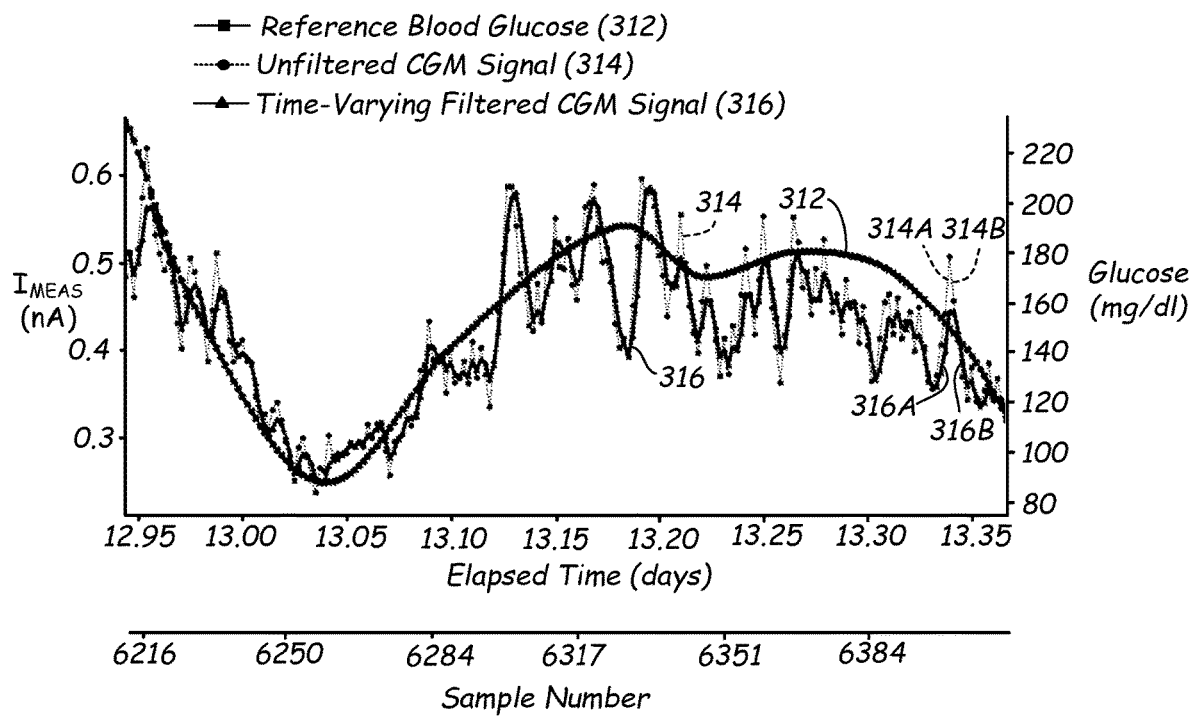
FIG. 3B is a graph illustrating an example of blood glucose concentrations of an individual, an unfiltered CGM signal, and a time-varying filtered CGM signal according to embodiments of the disclosure.

Additional reference is made to FIG. 3B, which is a graph showing an example of reference blood glucose concentrations 312, an unfiltered CGM signal 314, and a time-varying filtered CGM signal 316. The horizontal axis of the graph of FIG. 3B references elapsed time in days by sample number. It is noted that the examples shown in the graph of FIG. 3B are recorded during a portion of the analyte (e.g., glucose) monitoring period from the end of the twelfth day to about eight hours into the thirteenth day. The unfiltered CGM signal 314 may be an unfiltered CGM signal generated by the wearable device 102 (FIG. 1) and/or the external device 104 that measures and/or calculates analyte (e.g., glucose) concentrations of a user. The time-varying filtered CGM signal 316 may be generated by applying time-varying filtering to the unfiltered CGM signal 314 and/or one or more other signals used to generate the unfiltered CGM signal 314.

In some embodiments, one or more signals generated by biosensor(s) within the wearable device 102 may have the time-varying filtering applied thereto, which may yield the time-varying filtered CGM signal 316 (sometimes referred to as the filtered CGM signal 316). For example, the noisy signal 304 (FIG. 3A) may be a signal generated by a biosensor within the wearable device 102. The time-varying filtered CGM signal 316 may be the result of applying time-varying filtering to the noisy signal 304. As shown in FIG. 3B, the resulting time-varying filtered CGM signal 316 generally follows the reference blood glucose concentrations 312 and is much smoother than the unfiltered CGM signal 314 exhibiting more significant jitter.

Figure 4A:
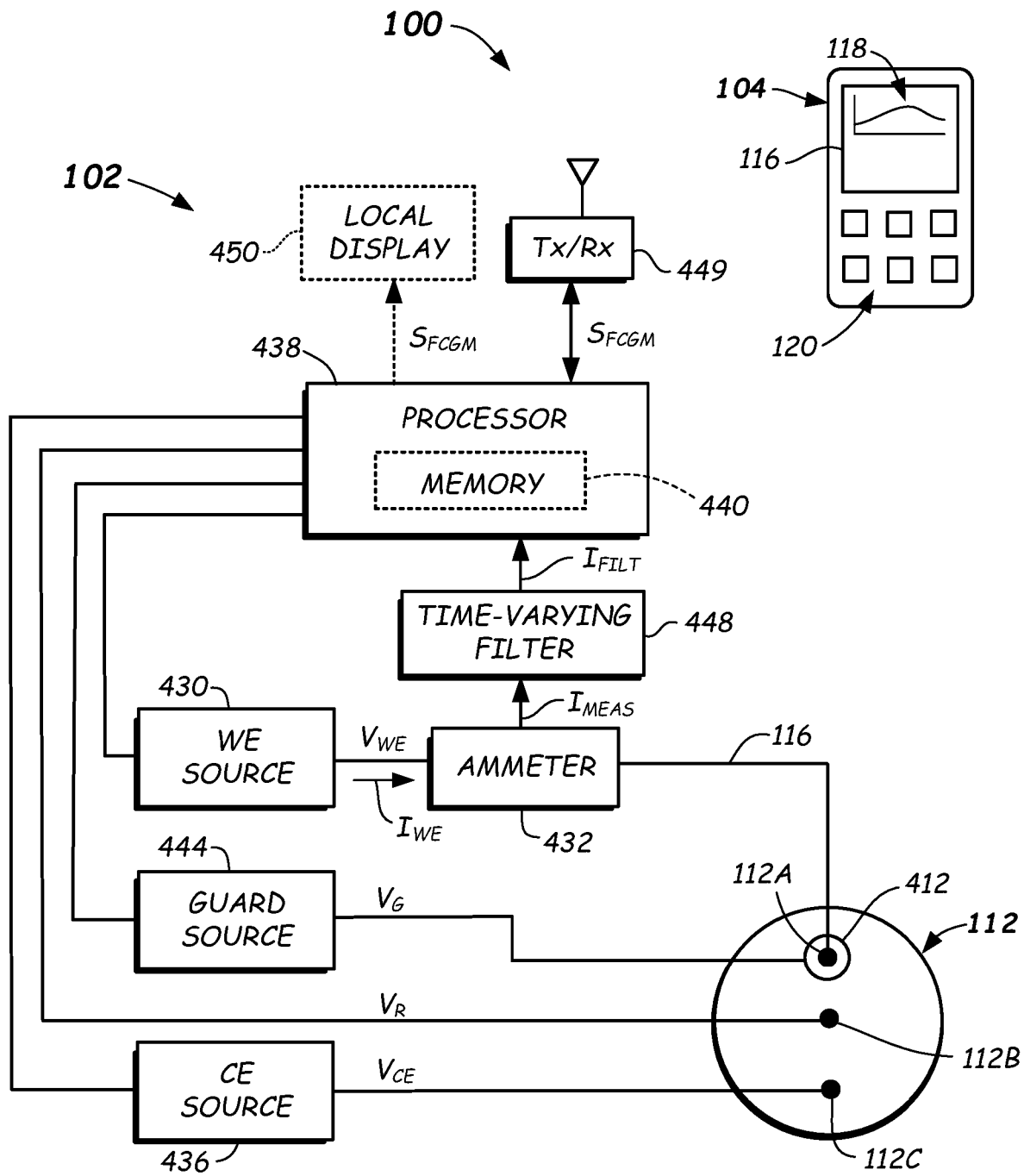
FIG. 4A is a schematic diagram showing an example of circuitry components within a wearable device of a CGM system according to embodiments of the disclosure.

Additional reference is now made to FIG. 4A, which illustrates a schematic diagram of an embodiment of example circuitry of the wearable device 102 (FIG. 2A). In the embodiment shown in FIG. 4A, the biosensor 112 does not include the background electrode 112D (FIG. 2B). As shown in FIG. 4A, the working electrode 112A may be surrounded by a guard ring 412 that reduces stray current from interfering with the working electrode 112A. In some embodiments, the guard ring 412 may operate at the same potential as the working electrode 112A. The working electrode 112A may be coupled to a working electrode source 430 by way of a current measuring device, such as an ammeter 432. The ammeter 432 measures a working electrode current $I_{WE}$ generated by the working electrode source 430 and generates the measured current signal $I_{MEAS}$, which is indicative of the working electrode current $I_{WE}$. During operation of the wearable device 102, the working electrode source 430 may generate a voltage $V_{WE}$ that is applied to the working electrode 112A resulting in the working electrode current $I_{WE}$ passing through the working electrode 112A. The ammeter 432 measures the working electrode current $I_{WE}$ and generates the measured current signal $I_{MEAS}$.

In the embodiment of FIG. 4A, the wearable device 102 may include a counter electrode source 436 electrically coupled to the counter electrode 112C that generates a counter electrode voltage $V_{CE}$. The working electrode current $I_{WE}$ is therefore proportional to the difference between the working electrode voltage $V_{WE}$ and the counter electrode voltage $V_{CE}$, divided by the impedances of the interstitial fluid 114 (FIG. 2) and the impedances of the electrodes in the biosensor 112. In some embodiments, a current sunk by the counter electrode source 436 is equal to the working electrode current $I_{WE}$.

Both the working electrode source 430 and the counter electrode source 436 may be coupled to and controlled by a processor 438. The processor 438 may include memory 440 having computer-readable instructions stored therein that cause the processor 438 to send instructions to the working electrode source 430 and the counter electrode source 436. The instructions may cause the working electrode source 430 and the counter electrode source 436 to output predetermined voltages (e.g., $V_{WE}$ and $V_{CE}$). The memory 440 may also include instructions that cause the processor to perform other functions as described herein, such as applying time-varying filtering.

The circuitry of the embodiment of the wearable device 102 shown in FIG. 4A may include a guard source 444 that is coupled to the guard ring 412 and supplies a guard voltage $V_G$ to the guard ring 412. The guard source 444 may also be coupled to the processor 438 and may receive instructions from the processor 438 to set a specific guard voltage $V_G$. The reference electrode 112B may be coupled to the processor 438 and may supply a reference voltage $V_R$ to the processor 438. The processor 438 may use the reference voltage $V_R$ to set values of the working voltage $V_{WE}$ and the counter voltage $V_{CE}$.

As described above, the ammeter 432 may generate the measured current signal $I_{MEAS}$, which is a measure of the working electrode current $I_{WE}$. In conventional CGM systems, if noise is present on the working electrode current $I_{WE}$, the measured current signal $I_{MEAS}$ and the resulting CGM signal may be noisy. For example, the resulting CGM signal may be similar to the unfiltered CGM signal 314 of FIG. 3B. In the embodiment of FIG. 4A, a time-varying filter 448 applies time-varying filtering to the measured current signal $I_{MEAS}$ prior to the measured current signal $I_{MEAS}$ being processed and/or received by the processor 438. The time-varying filter 448 outputs a filtered measured current signal $I_{FILT}$, which may be processed by the processor 438 to render the time-varying filtered CGM signal 316.

Figure 5A:
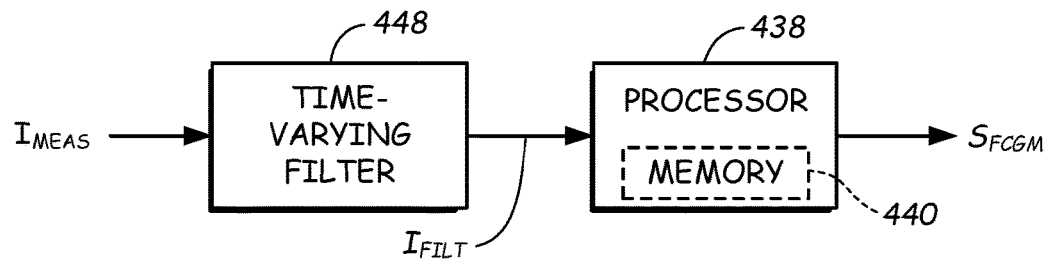
FIG. 5A is a block diagram showing an example of time-varying filtering in an embodiment of a wearable device of a CGM system according to embodiments of the disclosure.

Additional reference is made to FIG. 5A, which is a block diagram showing functions of a portion of the circuitry of FIG. 4A. As shown in the example of FIG. 5A, the time-varying filtering is applied by the time-varying filter 448 to the measured current signal $I_{MEAS}$ prior to the processor 438 processing the measured current signal $I_{MEAS}$. In other embodiments described herein, the time-varying filtering may be performed and/or applied by the processor 438 and/or to other signals within the external device 104 (FIG. 1).

The measured current signal $I_{MEAS}$ may be a noisy signal similar to the noisy signal 304 shown in FIG. 3A. As described herein, the biosensor 112 may degrade over time, which causes the noise level on the measured current signal $I_{MEAS}$ to increase as a function of time. If the processor 438 processes the noisy measured current signal $I_{MEAS}$, the resulting CGM signal may be corrupt and noisy (e.g., jittery) like the unfiltered CGM signal 314 shown in FIG. 3B. The filtered measured current signal $I_{FILT}$ output by the time-varying filter 448 is smoother (e.g., less noisy and/or jittery) than the measured current signal $I_{MEAS}$, so the resulting CGM signal is smoother. For example, the filtered measured current signal $I_{FILT}$ may be similar to the time-varying filtered signal 308 of FIG. 3A, which more closely follows an ideal measured current signal (e.g., without noise), such as the ideal signal 302 in FIG. 3A. The resulting CGM signal is similar to the time-varying filtered CGM signal 316 of FIG. 3B, which generally follows the reference blood glucose concentrations 312 and is much smoother than the unfiltered CGM signal 314. Thus, the time-varying filtering applied to the measured current signal $I_{MEAS}$ provides a CGM signal that more closely follows the blood glucose levels of the user and may be easier for the user of the wearable device 102 (FIG. 1) to interpret.

Embodiments of the time-varying filter 448 include analog and digital filters. In some embodiment, the time-varying filter 448 may be an analog or digital low-pass filter. In some embodiments, the time-varying filter 448 may be an infinite impulse response (IIR) filter or a finite impulse response filter (FIR). In some embodiments, the time-varying filter 448 may apply an exponential moving average (EMA) to the measured current signal $I_{MEAS}$ or other signals. The attenuation of the low-pass filter may increase as a function of time such that greater attenuation is achieved later in the analyte (e.g., glucose) monitoring period. In some embodiments, the time-varying filter 448 may be an analog low-pass filter, wherein the order of the low-pass filtering may increase as a function of time. In some embodiments, the cut-off frequency or frequencies of the time-varying filter 448 may change as a function of time.

Figure 5B:
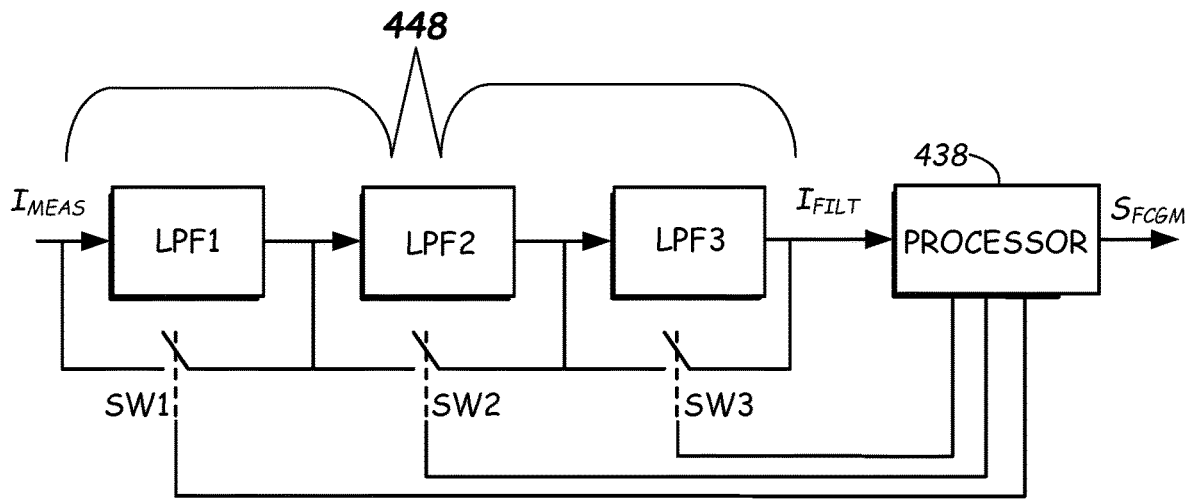
FIG. 5B is a schematic diagram of a time-varying filter implemented as a plurality of low-pass filters coupled in series according to embodiments of the disclosure.

Additional reference is made to FIG. 5B, which illustrates an example of the time-varying filter 448 implemented as a plurality of low-pass filters, such as in a filter bank, which are referenced individually as a first low-pass filter LPF1, a second low-pass filter LPF2, and a third low-pass filter LPF3, coupled in series. The time-varying filter 448 may include fewer or more low-pass filters. The time-varying filter 448 may also include a switch (SW) coupled in parallel with each of the low-pass filters LPF1, LPF2, LPF3. In the embodiment of FIG. 5B, the switches are referred to individually as a first switch SW1, a second switch SW2, and a third switch SW3. The states of the switches SW1, SW2, SW3 may be controlled by the processor 438. The amount of time-varying filtering applied by the time-varying filter 448 may be adjusted by opening or closing the switches SW1, SW2, SW3. For example, during a first time period all the switches SW1, SW2, and SW3 may be closed so no filtering is applied. During subsequent time periods, switches may be opened to apply progressively more filtering as a function of time.

Figure 6:
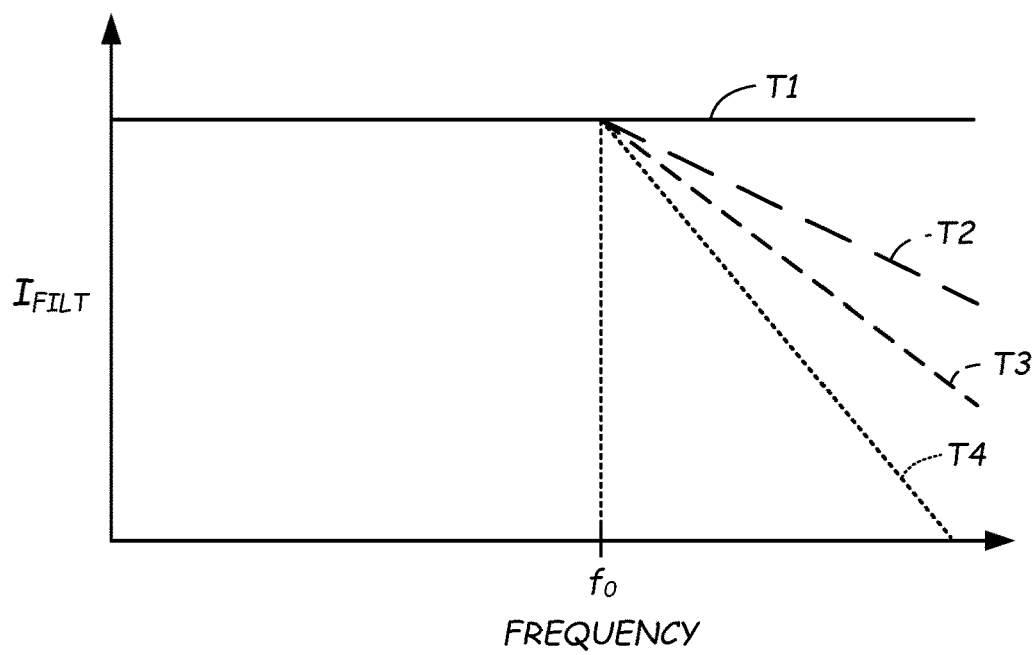
FIG. 6 is a graph showing example time-varying filter responses versus frequency over different time periods (T1 through T4) according to embodiments described herein.
Figure 7:
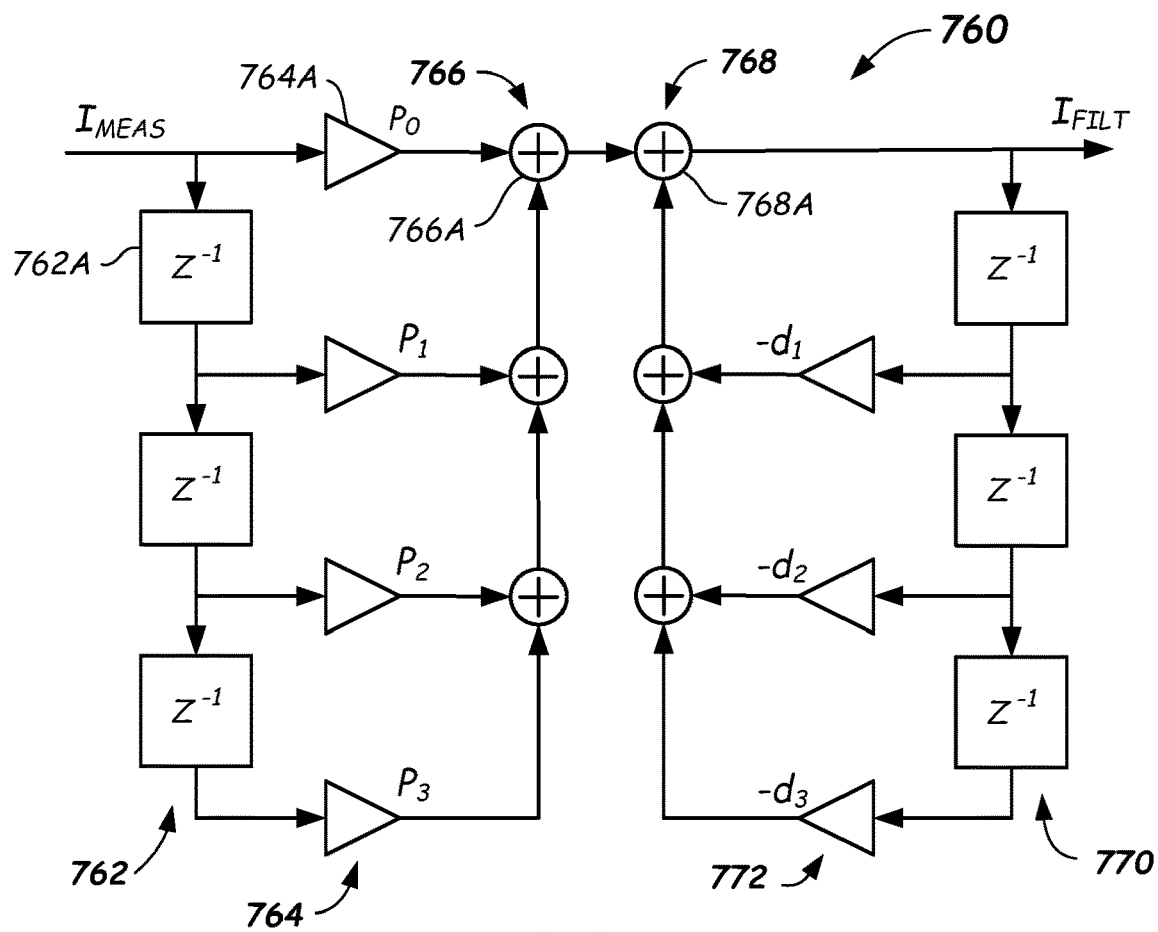
FIG. 7 illustrates a block diagram of an example of an infinite impulse response filter according to embodiments of the disclosure.

Additional reference is made to FIG. 6, which is a graph showing example filter responses over time for the time-varying filter 448, wherein the time-varying filter 448 is a low-pass filter having a cutoff frequency $f_0$. The graph of FIG. 6 is described below with reference to the time-varying filter 448 of FIG. 5B. However, other time-varying filters, such as time-varying IIR filters may produce similar results.

During a first period T1, no filtering may be applied by the time-varying filter 448. For example, early during a glucose monitoring period, no filtering may be required. The elapsed time of no filtering is thus the first period T1. During a second period T2, the time-varying filter 448 may function as a first order low-pass filter. The elapsed time of the second period T2 may commence at a predetermined period after the start of the glucose monitoring period. In some embodiments, the second period T2 may commence after the start of the glucose monitoring period, such as at least twenty-four hours after the start of the glucose monitoring period. The elapsed time of the second period T2 may commence after the end of the first period T1 and may end at the start of a third period T3. As shown in FIG. 6, the attenuation in the stop band is minimal during the second period T2. The filtering shown during the second period T2 may be achieved by opening one of the switches, such as SW-1.

During a third period T3, which may follow the second period T2, the low-pass filter may be a higher order filter than during the first period T1. With regard to the time-varying filter 448 of FIG. 5B, two switches, such as switches SW-1 and SW-2 may be opened by the processor 438. The elapsed time of the third period may commence at the end of the second period and may end at the beginning of a fourth period T4. During a fourth period T4, the time-varying filter 448 may be a higher order low-pass filter than during the third period T3. During the fourth period T4, the processor may open all the switches SW-1, SW-2, and SW-3. The elapsed time of the fourth period T4 may commence at the end of the third period T3 and may end at the end of the monitoring period.

The time-varying filter 448 may increase the order of the low-pass filtering as a function of time. In some embodiments, the cutoff frequency $f_0$ may change with each different period. For example, higher noise levels on the signals may include higher or lower frequency components. The cutoff frequency $f_0$ may change as the frequency components of the noise change.

In some embodiments, the time-varying filter 448 may be a digital filter, such as a FIR (finite impulse response) filter or an IIR (infinite impulse response) filter, for example. Other types of digital filters may be used. Additional reference is made to FIG. 7, which is a block diagram of an example embodiment of an IIR filter 760 that may be used in the time-varying filter 448. Other configurations of digital filters and IIR filters may be used. The IIR filter 760 receives the measured current signal $I_{MEAS}$ (or another signal), which is a digital signal. In some embodiments, the ammeter 432 (FIG. 4A) generates the digital signal and in other embodiments, the circuitry of FIG. 4A includes an analog-to-digital converter (not shown) that can digitize the measured current signal $I_{MEAS}$. In other embodiments, the IIR filter 760 may be used to filter other signals, such as an unfiltered CGM signal, in the CGM system 100 (FIG. 1).

The measured current signal $I_{MEAS}$ is received into a feedforward side of the IIR filter 760 at a first unit delay 762A of a series of unit delays 762 and a first multiplier 764A of a series of multipliers 764. The outputs of the multipliers 764 are output to a plurality of adders 766, including a first adder 766A. The output of the first adder 766A is input to a first adder 768A of a series of adders 768 on the feedback side of the IIR filter 760. The output of the first adder 768A is the output of the IIR filter 760. The output is fed to a series of unit delays 770, which output to a series of multipliers 772. The outputs of the multipliers 772 are input to the adders 768. The filtering of the IIR filter 760 is established by the coefficients $P_0$-$P_3$ of the multipliers 764 and coefficients $-d_1$ to $-d_3$ of the multipliers 772, which may be time-varying to provide the time-varying filtering described herein.

Other embodiments of time-varying filtering are described below with respect to a generic signal S(t) in the CGM system 100. In these embodiments, a filter F is applied to the signal S(t) to obtain a smoother output S' as follows:

$$S'(t)=F(S(t)) \quad \text{Equation (1)}$$

In the embodiment of FIG. 4A, the filter F may be the time-varying filter 448 and the signal S(t) may be the measured current signal $I_{MEAS}$, an unfiltered CGM signal, or another signal for example. In time-varying filtering, the filter F may be dependent on time t, so that Equation (1) yields Equation (2) as follows:

$$S'(t)=F(t,S(t)) \quad \text{Equation (2)}$$

The time-varying filtering of Equation (2) may yield Equation (3) as follows for an exponential smoothing filter:

$$S'(t)=\text{alpha}*S(t)+(1-\text{alpha})*S'(t-1) \quad \text{Equation (3)}$$

wherein alpha is a value less than or equal to 1.0. When alpha equals 1.0, there is no smoothing (e.g., filtering) of the signal S(t). As alpha is reduced over time, the filter smooths the signal S(t).

In embodiments where the time-varying filter 448 is a digital filter, such as an IIR filter, and the signal S is a digital signal S(n), Equation (2) may be written in the discrete domain as F(n, S(n)) as shown in Equation 4 as follows:

$$S'(n)=\text{alpha}*S(n)+(1-\text{alpha})*S'(n-1) \quad \text{Equation (4)}$$

The smoothing may be applied by way of an exponential moving average (EMA). There are variations of the filtering/smoothing method. Two variations are referred to as DEMA and TEMA (double and triple EMA, respectively) that may be used in the time-varying filter 448. To make the filtering change with time, alpha may be made to change as a function of time. In some embodiments, alpha is made to decrease steadily as elapsed time from the start of the glucose monitoring period increases as described below in Equation (5):

$$\text{alpha}(t)=\text{baseAlpha}-t/N \quad \text{Equation (5)}$$

wherein t is time and baseAlpha may be a predetermined value and may be a nominal (e.g., maximum) value of alpha that may be determined during design of the wearable device 102 (FIG. 1) and which, in some embodiments, may never change. N is a constant used to control the rate of change of alpha(t). In some embodiments, baseAlpha may range from about 0.3 to about 0.5 and N may be chosen so that alpha(t) is less than or equal to baseAlpha/2 when t is greater than seven days. Other values of baseAlpha, t, and/or N and adjustments thereto may be used. Accordingly, in some embodiments, more smoothing is applied as time increases. In some embodiments, the increased smoothing is applied on a steady, linear schedule. In other embodiments, the increased smoothing is applied nonlinearly, such as in a stepwise fashion or as a non-linear function. In some embodiments, alpha(n) may be used instead of alpha(t), wherein n is a sample number.

In some embodiments, alpha(t) may be greater than a minimum value to prevent too much smoothing. In other embodiments, alpha(t) may vary in a non-linear way with time, or be restricted to certain time periods, etc. In some examples, the smoothing or filtering may commence at a fixed time after the glucose monitoring period starts. In some embodiments, the smoothing or filtering may commence at least twenty-four hours after the start of the glucose monitoring period. In some embodiments, the filtering may be applied to any or all of the following: working electrode current $I_{WE}$, current through the reference electrode, the CGM signal, the measured current signal $I_{MEAS}$, and/or the like, for example.

Referring again to the circuitry of FIG. 4A, the processor 438 may receive the filtered measured current signal $I_{FILT}$ and calculate the CGM signal based at least in part on the filtered measured current signal $I_{FILT}$. For example, instructions (e.g., programs) stored in the memory 440 may cause the processor 438 to process the filtered measured current signal $I_{FILT}$ to calculate or estimate the glucose concentration in the interstitial fluid 114 (FIG. 2) and generate the filtered CGM signal $S_{FCGM}$. The filtered CGM signal may reflect other analytes and may be referred to as a time-varying filtered CAM signal. Because the filtered measured current signal $I_{FILT}$ is smoothened, the resulting filtered CGM signal $S_{FCGM}$ will also be smoothened relative to a CGM signal calculated using an unfiltered current measurement signal such as the measured current signal $I_{MEAS}$. In some embodiments, the time-varying filter 448 may filter the measured current signal $I_{MEAS}$ and another time-varying filter implemented in the processor 438 may further filter or smooth the CGM signal to produce the final filtered CGM signal $S_{FCGM}$.

The filtered CGM signal $S_{FCGM}$ may be output by the processor 438 to a transmitter/receiver 449. The transmitter/receiver 449 may transmit the filtered CGM signal $S_{FCGM}$ to an external device, such as the external device 104 for processing and/or display on the external display 116. In some embodiments, the processor 438 may transmit the filtered CGM signal $S_{FCGM}$ to an optional local display 450 located on the wearable device 102 wherein the filtered CGM signal $S_{FCGM}$ and/or other information can be displayed.

Figure 4B:
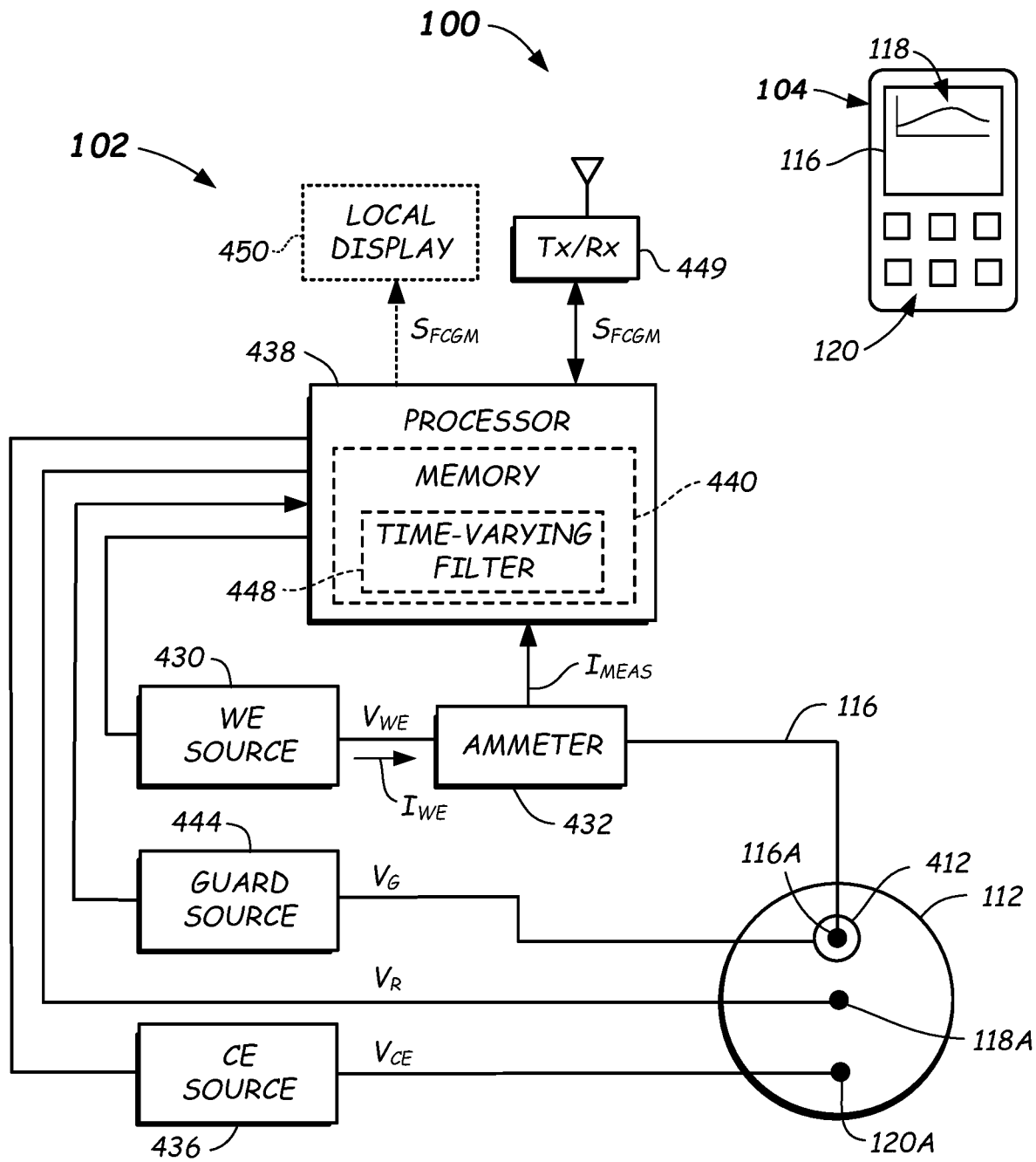
FIG. 4B is a schematic diagram showing an example of circuitry components within a wearable device that can communicate with an external device of a CGM system according to embodiments of the disclosure.
Figure 5C:
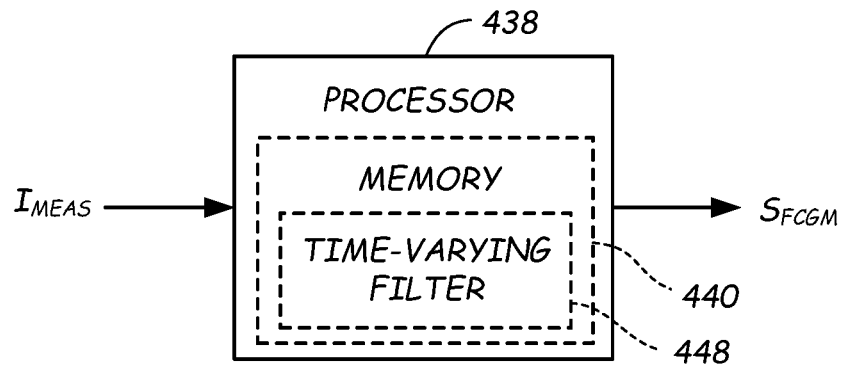
FIG. 5C is a block diagram showing an example of signal processing including time-varying filtering in an embodiment of a wearable device of a CGM system according to embodiments of the disclosure.

Reference is now made to FIG. 4B, which illustrates another embodiment of circuitry that may be configured in the wearable device 102 (FIG. 1). In the embodiment of FIG. 4B, the time-varying filter 448 is implemented in the processor 438. For example, the time-varying filter 448 may be a digital filter wherein instructions for time-varying filtering are stored in the memory 440 and executed by the processor 438. The processor 438 may apply the time-varying filtering or smoothing described in Equation (4) to the measured current signal $I_{MEAS}$ and/or an unfiltered CGM signal. The filtered CGM signal $S_{FCGM}$ may be output to the transmitter/receiver 449 to be transmitted to an external device, such as the external device 104. The filtered CGM signal $S_{FCGM}$ may also be transmitted to the optional local display 450 for display as described above. A block diagram of the time-varying filtering of the embodiment of FIG. 4B is shown in FIG. 5C. As shown in FIG. 5C, the measured current signal $I_{MEAS}$ is received and processed by the processor 438, which outputs the filtered CGM signal $S_{FCGM}$.

The time-varying filter 448 may be implemented in the processor 438 as described above. Accordingly, the time-varying filter 448 may apply a smoothing function as described in Equation (4). The time-varying filter 448 may implement a FIR filter or an IIR filter as described above.

Figure 4C:
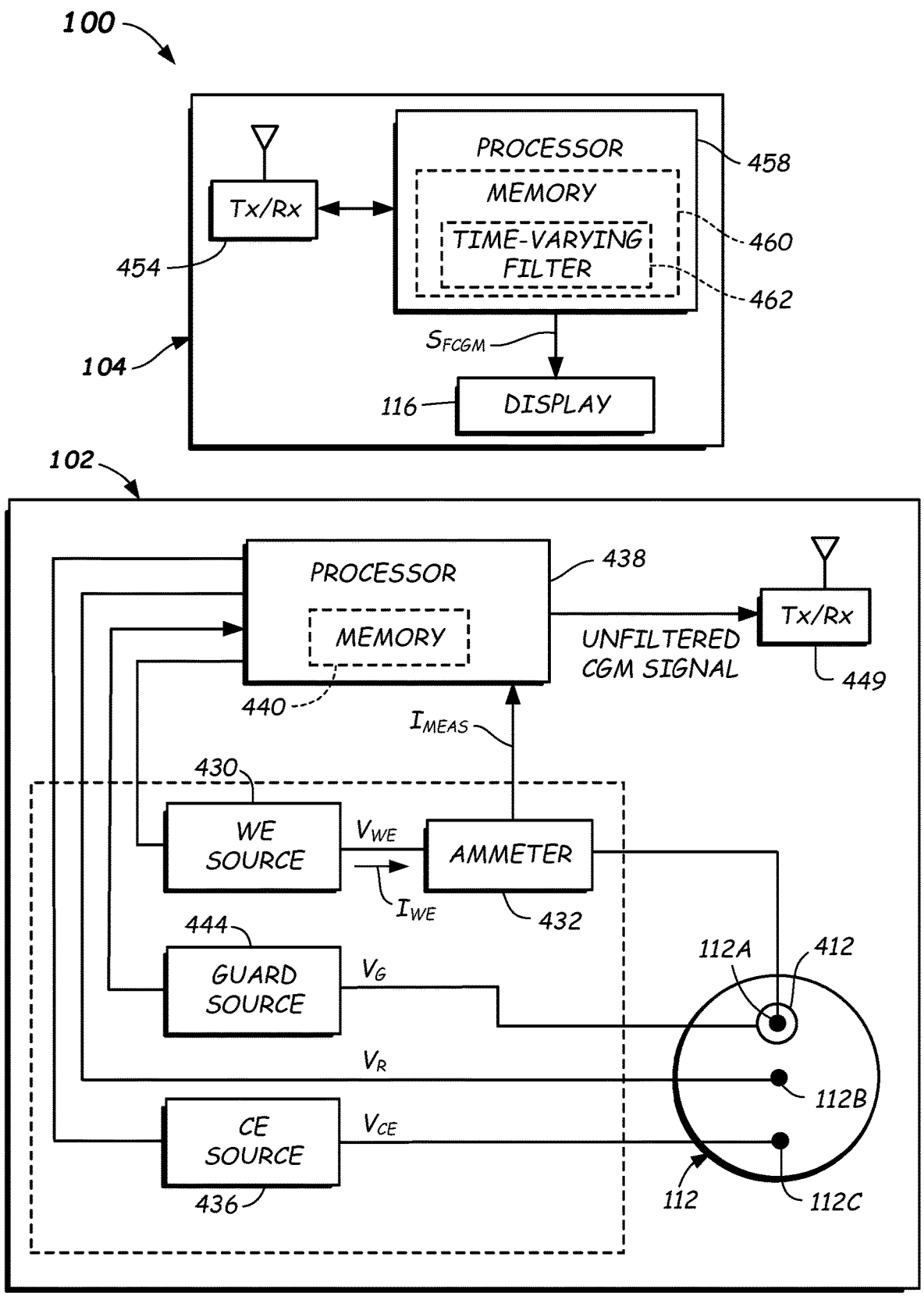
FIG. 4C is a schematic diagram showing another example of circuitry within a wearable device and an external device of a CGM system according to embodiments of the disclosure.

Reference is now made to FIG. 4C, which illustrates another embodiment of example circuitry in the CGM system 100 including the wearable device 102 and the external device 104. In the embodiment of FIG. 4C, the time-varying filtering is at least partially implemented in the external device 104 as described herein. In the embodiment of FIG. 4C, the external device 104 may include a transmitter/receiver 454, an external display 116, a processor 458, memory 460, and a time-varying filter 462 that may be stored in the memory 460 and implemented (e.g., executed) by the processor 458. In some embodiments, the transmitter/receiver 454 may receive an unfiltered CGM signal from the transmitter/receiver 449 located in the wearable device 102. In some embodiments, the transmitter/receiver 449 and the transmitter/receiver 454 may communicate wirelessly, such as by BLUETOOTH® or other suitable communication protocol. The transmitter/receiver 454 may also transmit instructions to the wearable device 102.

The time-varying filter 462 may be a digital filter wherein instructions for the time-varying filtering are stored in the memory 460 and executed by the processor 458 in the same or similar manner as described in connection with FIG. 4B. As described above, the time-varying filtering may be applied to the unfiltered CGM signal transmitted from the wearable device 102. In some embodiments, the external device 104 may receive the measured current signal $I_{MEAS}$ and the time-varying filter 462 may process the measured current signal $I_{MEAS}$ as described in connection with FIGS. 4A and 4B to generate a filtered CGM signal $S_{FCGM}$. For example, the time-varying filter 462 may generate a signal similar to $I_{FILT}$, which may be processed by the processor 458 to generate the filtered CGM signal $S_{FCGM}$. The filtered CGM signal $S_{FCGM}$ and/or other data calculated by the processor 458 may be output to the external display 116 and/or otherwise downloaded to another device (e.g., computer).

Figure 5D:
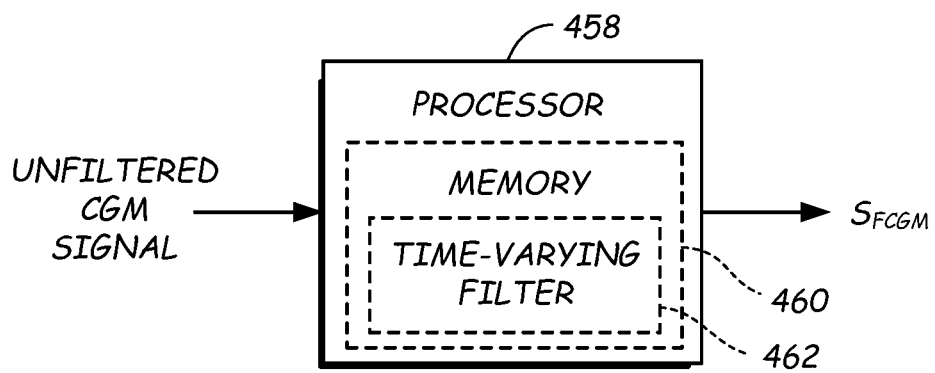
FIG. 5D is a block diagram showing an example of signal processing in an embodiment of a CGM system, wherein at least some of the time-varying filtering is performed in an external device according to embodiments of the disclosure.
Figure 5E:
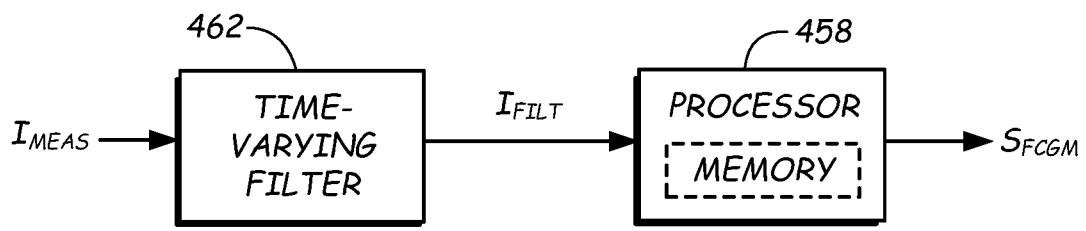
FIG. 5E is a block diagram showing another example of signal processing in an embodiment of a CGM system, wherein at least some of the time-varying filtering is performed in an external device according to embodiments of the disclosure.

Block diagrams of the time-varying filtering of the embodiment of FIG. 4C are shown in FIGS. 5D and 5E. As shown in FIG. 5D, the unfiltered CGM signal is received by the processor 458, which executes the time-varying filter 462 to generate the filtered CGM signal $S_{FCGM}$. The unfiltered CGM signal may be received from the wearable device 102. In FIG. 5E, the measured current signal $I_{MEAS}$ is received in the external device 104 and input to the time-varying filter 462. The time-varying filter 462 outputs the filtered measured current signal $I_{FILT}$, which is processed by the processor 458 to generate the filtered CGM signal $S_{FCGM}$.

In each of the embodiments, the optional local display 450 and/or the external display 116 may display graphs and/or numbers indicative of glucose concentrations. The information displayed may also include trends in glucose concentrations, such as downward and upward trends (e.g., displayed as an upwards or downwards arrow). Other information may also be displayed, such as units. Because the filtered CGM signal $S_{FCGM}$ has been filtered by the time-varying filtering, the graphs and/or other information are more accurate than conventional information displayed for users. An example of the greater accuracy of information provided by the filtered CGM signals $S_{FCGM}$ is shown by the time-varying filtered CGM signal 316 in FIG. 3B.

Examples of filtering and/or smoothing are described in the examples below. Portions 314A and 314B of the unfiltered CGM signal 314 shown in FIG. 3B are in the thirteenth day of the CGM monitoring period and contain significant noise. For example, the portion 314A indicates that the user's glucose concentration is rising from about 125 mg/dl to about 180 mg/dl over a period of approximately four samples. The portion 314B indicates that the user's glucose concentration is falling from 180 mg/dl to about 120 mg/dl during the next four samples. The reference blood glucose concentrations 312 indicates that the user's glucose concentration is falling from about 150 mg/dl to about 145 mg/dl during the eight samples of the portion 314A and the portion 314B combined. If the user relies on the unfiltered CGM information in the portion 314A, the user will be informed that the glucose concentration is rising rapidly, when in reality the glucose concentration is actually declining slightly. Should the user rely on the information in the portion 314B, the user can be informed that the glucose concentration is rapidly declining, when in reality the glucose concentration is slowly declining.

The filtered CGM signal $S_{FCGM}$ 316 includes a portion 316A and a portion 316B that reflect glucose concentrations of the filtered CGM signal $S_{FCGM}$ 316 during the same sampling times as the portion 314A and the portion 314B, respectively. As shown in FIG. 3B, the filtered CGM signal $S_{FCGM}$ 316 rises from about 125 mg/dl to about 155 mg/dl during the portion 316A and falls from about 155 mg/dl to about 125 mg/dl during the portion 316B. The changes in glucose concentrations provided by the filtered CGM signal $S_{FCGM}$ 316 are not as steep as those provided by the unfiltered CGM signal 314. Thus, information provided to the user may more accurately reflect the true glucose concentrations. For example, the rise in glucose concentration shown in the portion 316A and the subsequent fall in glucose concentration shown in the portion 316B are not as severe as those shown in the unfiltered CGM signal 314 and more closely follow the reference blood glucose concentrations 312. Thus, the use of time-varying filtering in a CGM system increases the reliability of data, including the CGM signal, generated by the CGM system.

Reference is made to Table 1 below, which summarizes results for various filtering options. MARD, as used in Table 1, is the mean absolute relative difference. A static filter includes a filter wherein the attenuation of the filter remains constant as a function of time.

For CGM glucose determinations, the MARD is described by Equation (6) as follows:

$$\text{MARD} = 100 * \Sigma[\text{Abs}([G_{CGM} - G_{REF}]/G_{REF})]/n) \quad \text{Equation (6)}$$

wherein $G_{CGM}$ is the CGM measured glucose concentration, $G_{REF}$ is a reference glucose concentration, measured by blood glucose measurement (BGM), for example, and n is the number of data points. The expression of MARD combines the mean and standard deviation of a sample population against the reference glucose values to produce a composite MARD value, where the smaller the MARD value, the better the accuracy. In some embodiments, a 10% MARD value may have an approximate accuracy of data within ±25%, or an approximate 25% accuracy. Conversely, a CGM system having an accuracy of ±10% would be projected to have a MARD value of 4%. As shown in Table 1, embodiments described herein using time-variable filtering are roughly comparable MARD values of conventional filtering.

TABLE 1

Data Comparisons

| Parameter | No Filtering | Static Filtering | Time-Varying Filtering |
|---|---|---|---|
| MARD 0-7 days | 13.75 | 13.89 | 14.06 |
| MARD 0-10 days | 13.73 | 13.90 | 14.03 |
| Smoothness 0-10 days | 0.154 | 0.118 | 0.107 |
| Smoothness 7-10 days | 0.194 | 0.143 | 0.125 |

The smoothness may be calculated using different techniques. For example, smoothness may be calculated using the arithmetic average method. In other embodiments, smoothness may be calculated as the standard deviation of the glucose differences divided by the absolute value of the mean of the glucose differences. Other methods may be used to calculate the smoothness. As shown in Table 1, the signals having time-varying filtering applied thereto are smoother than conventional signals.

The CGM has been described as using devices that include biosensors located in interstitial fluid. Other CGM devices may be used. For example, optical sensors may also be used for continuous glucose or analyte monitoring. The optical device may employ fluorescence, absorbance, reflectance, and/or the like to measure glucose or other analytes. For example, an optical oxygen sensor relying on fluorescence or quenching of fluorescence may be employed to indirectly measure glucose by measuring the oxygen concentration in interstitial fluid, which has an inverse relationship to the glucose concentration.

Figure 8:
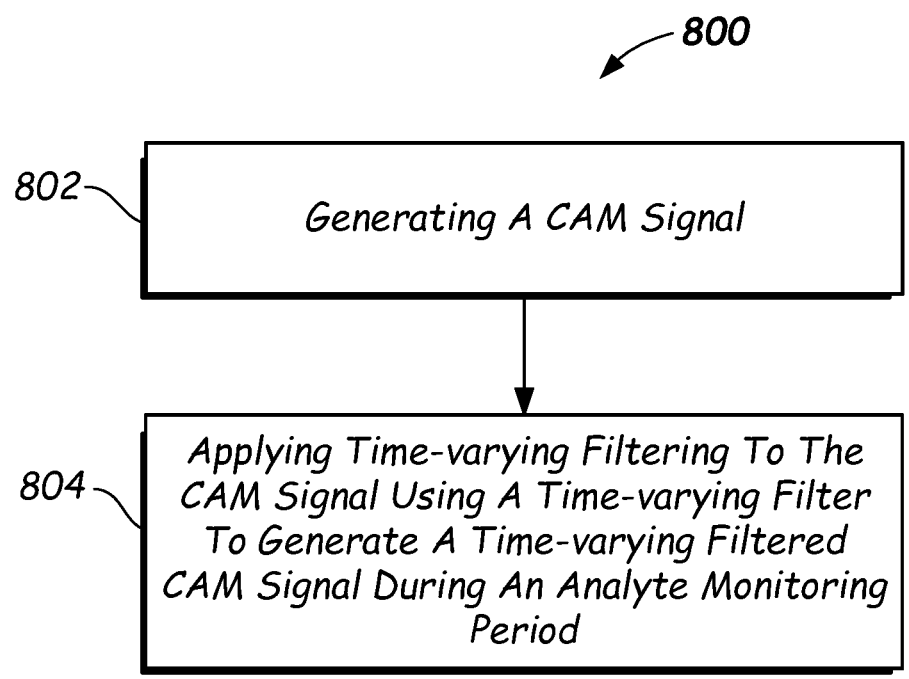
FIG. 8 illustrates a flowchart of a method of filtering a signal in a CAM system according to embodiments of the disclosure.

Reference is now made to FIG. 8, which illustrates a flowchart depicting a method 800 of filtering a continuous analyte monitoring (CAM) signal. Filtering a continuous glucose monitoring (CGM) signal is one example. Other suitable analytes may be monitored, such as lactate. The method 800 includes, in 802, generating a CAM signal. The method 800 includes, in 804, applying time-varying filtering to the CAM signal using a time-varying filter (e.g., time-varying filter 448, 462) to generate a time-varying filtered CGM signal (e.g., time-varying filtered CGM signal $S_{FCGM}$ 316) during an analyte monitoring period.

As discussed above, there are two general types of time-varying filtering: 1) where a signal within the CGM system 100, such as the measured current $I_{MEAS}$, is time-varying filtered and further processed to produce a filtered CGM signal $S_{FCGM}$, which may be transferred by the transmitter/receiver 449 to the external device 104, and 2) where $I_{MEAS}$ is processed to generate an unfiltered CGM signal, which is further processed to produce the filtered CGM signal $S_{FCGM}$.

The foregoing description discloses only example embodiments. Modifications of the above-disclosed apparatus and methods which fall within the scope of this disclosure will be readily apparent to those of ordinary skill in the art.

What is claimed is:

1. One or more non-transitory computer-readable media comprising computer-executable instructions that, when executed by at least one processor, perform a method of filtering a signal in a continuous analyte monitoring system during an analyte monitoring period, the method comprising:
applying a time-varying filter to the signal to smooth the signal, wherein the signal is generated by a biosensor during the analyte monitoring period and the analyte monitoring period comprises a plurality of distinct time periods,
wherein the time-varying filter comprises:
a plurality of low-pass filters and a plurality of switches, each of the plurality of switches being coupled in parallel to at least one of the plurality of low-pass filters,
wherein for each distinct time period of the plurality of distinct time periods, the time-varying filter applies a level of filtering to the signal,
wherein the applying the level of filtering comprises:
opening an additional one of the plurality of switches for each distinct time period such that an additional one of the plurality of low-pass filters applies the level of filtering relative to an immediately prior level of filtering corresponding to an immediately prior time period,
wherein the addition of one of the plurality of low-pass filters increases the level of filtering applied relative to the immediately prior level of filtering corresponding to an immediately prior time period.

2. The method of claim 1,
wherein applying the time-varying filter to the signal further comprises:
passing the signal through at least one of the plurality of low-pass filters; and
applying the level of filtering to the signal for each distinct time period of the plurality of distinct time periods,
wherein for each level of filtering for each distinct time period, a level of attenuation in a stop band of the at least one of the plurality of low-pass filters is increased relative to an immediately prior level of attenuation in a stop band of the at least one of the plurality of low-pass filters corresponding to an immediately prior time period.

3. The method of claim 2,
wherein the time-varying filter comprises a finite impulse response filter.

4. The method of claim 1,
wherein the signal is a measured current signal, and the applying the time-varying filter to the signal further comprises:
calculating analyte concentrations from the measured current signal;
generating a continuous analyte monitoring signal from the analyte concentrations; and
applying the time-varying filter to the continuous analyte monitoring signal to produce a filtered continuous analyte monitoring signal during the analyte monitoring period.

5. The method of claim 4, further comprising:
displaying at least a portion of the filtered continuous analyte monitoring signal on a display;
analyzing the filtered continuous analyte monitoring signal to generate a trend in analyte concentrations during the analyte monitoring period; and
displaying the trend in the analyte concentrations on the display.

6. The method of claim 4,
wherein the applying the time-varying filter to the signal further comprises applying the level of filtering in a form of:
$S'(n) = alpha(t)*S(n)+(1-alpha(t))*S'(n-1)$ wherein S'(n) is the filtered continuous analyte monitoring signal, S(n) is the signal, alpha(t) is a value less than or equal to 1.0, t is time, and n is a sample number.

7. The method of claim 6,
wherein for each level of filtering for each distinct time period, the value of alpha(t) is decreased relative to an immediately prior value of alpha(t) corresponding to an immediately prior time period, such that alpha(t) consistently decreases as elapsed time increases during the analyte monitoring period.

8. The method of claim 1,
wherein the signal is a measured current signal, and the applying the time-varying filter to the signal further comprises:
applying the time-varying filter to the measured current signal to produce a filtered measured current signal during the analyte monitoring period;
calculating analyte concentrations from the filtered measured current signal; and
generating a filtered continuous analyte monitoring signal from the analyte concentrations.

9. The method of claim 1,
wherein the time-varying filter comprises an infinite impulse response filter.

10. The method of claim 1,
wherein applying the time-varying filter to the signal further comprises:
applying an exponential moving average to the signal.

11. The method of claim 1,
wherein the time-varying filter is an analog low-pass filter and the applying the time-varying filter further comprises:
passing the signal through an analog low-pass filter; and
applying the level of filtering to the signal for each distinct time period of the plurality of distinct time periods,
wherein for each level of filtering for each distinct time period, an order of low-pass filtering is increased relative to an immediately prior order of low-pass filtering corresponding to an immediately prior time period.

12. The method of claim 1,
wherein the plurality of low-pass filters are coupled in series.

13. One or more non-transitory computer-readable media comprising computer-executable instructions that, when executed by at least one processor, perform a method of filtering a signal over an analyte monitoring period, the method comprising:
identifying a first time period occurring during the analyte monitoring period,
wherein the first time period begins proximate to a start of the analyte monitoring period;
applying a first level of filtering to the signal during the first time period;
identifying a second time period occurring during the analyte monitoring period, wherein the second time period begins after an end of the first time period;
applying a second level of filtering to the signal during the second time period,
wherein the second level of filtering is an increased level of filtering relative to the first level of filtering, wherein applying the second level of filtering comprises:
opening a first switch in a time-varying filter such that a first low-pass filter comprised in the time-varying filter applies the second level of filtering to the signal, the first switch being coupled in parallel with the first low-pass filter;
identifying a third time period occurring during the analyte monitoring period, wherein the third time period begins after an end of the second time period;
applying a third level of filtering to the signal during the third time period,
wherein the third level of filtering is an increased level of filtering relative to the first level of filtering and the second level of filtering;
identifying subsequent time periods occurring sequentially after the third time period and during the analyte monitoring period,
wherein the subsequent time periods begin sequentially after an end of the third time period; and
applying increased levels of filtering to the signal during the subsequent time periods, wherein for each level of filtering for each subsequent time period, the level of filtering is increased relative to an immediately prior level of filtering corresponding to an immediately prior time period to thereby provide consistently increased levels of filtering of the signal across the subsequent time periods.

14. The method of claim 13,
wherein the second time period begins at least 24 hours after the start of the analyte monitoring period.

15. The method of claim 13,
wherein applying increased levels of filtering to the signal during the subsequent time periods further comprises:
passing the signal through at least one low-pass filter; and
applying increased levels of attenuation in a stop band of the at least one low-pass filter during the subsequent time periods,
wherein for each level of filtering for each subsequent time period, a level of attenuation in a stop band of the at least one low-pass filter is increased relative to an immediately prior level of attenuation in a stop band of the at least one low-pass filter corresponding to an immediately prior time period to thereby provide consistently increased levels of attenuation in a stop band of the at least one low-pass filter across the subsequent time periods.

16. the method of claim 13,
wherein the signal is a measured current signal, and the applying increased levels of filtering to the signal during the subsequent time periods further comprises:
calculating analyte concentrations from the measured current signal;
generating a continuous analyte monitoring signal from the analyte concentrations; and
applying the increased levels of filtering to the continuous analyte monitoring signal to produce a filtered continuous analyte monitoring signal during the subsequent time periods occurring in the analyte monitoring period.

17. The method of claim 16,
wherein the applying increased levels of filtering to the continuous analyte monitoring signal during the subsequent time periods occurring in the analyte monitoring period further comprises applying increased levels of filtering in a form of:
$S'(t) = alpha(t)*S(t) + (1 - alpha(t))*S'(n-1)$,
wherein S'(t) is a filtered continuous analyte monitoring (CAM) signal, S(t) is the CAM signal, alpha(t) is a value less than or equal to 1.0, and t is time.

18. The method of claim 17,
wherein for each level of filtering for each subsequent time period, the value of alpha(t) is decreased relative to an immediately prior value of alpha(t) corresponding to an immediately prior time period to thereby provide consistently increased levels of filtering of the signal as elapsed time increases in the analyte monitoring period.

19. The method of claim 13,
wherein the time-varying filter is a first order low-pass filter during the second time period.

20. The method of claim 19,
wherein applying the third level of filtering to the signal during the third time period further comprises:
opening a second switch in the time-varying filter, in addition to the first switch being opened,
wherein the second switch is coupled in parallel with a second low-pass filter comprised in the time-varying filter, and
wherein opening the second switch in addition to the first switch being opened causes the first low-pass filter and the second low-pass filter to cooperatively apply the third level of filtering to the signal, thereby increasing the level of filtering relative to the first level of filtering and the second level of filtering.

21. The method of claim 20,
wherein the time-varying filter is a second order low-pass filter during the third time period.

22. The method of claim 13,
wherein the first level of filtering applied to the signal during the first time period is no filtering.

23. The method of claim 13,
wherein the signal is a measured current signal, and the applying increased levels of filtering to the signal during the subsequent time periods further comprises:
applying the increased levels of filtering to the measured current signal to produce a filtered measured current signal during the analyte monitoring period;
calculating analyte concentrations from the filtered measured current signal; and
generating a filtered continuous analyte monitoring signal from the analyte concentrations.

24. The method of claim 23, further comprising:
transmitting the filtered continuous analyte monitoring signal to an external device for display of the filtered continuous analyte monitoring signal.

25. The method of claim 13,
wherein the applying the levels of filtering to the signal comprises applying infinite impulse response filtering to the signal.

26. A continuous analyte monitoring (CAM) system, comprising:
a wearable device, the wearable device comprising:
a biosensor, wherein the biosensor generates a signal during an analyte monitoring period, the analyte monitoring period comprising a first time period and a plurality of subsequent time periods,
wherein the plurality of subsequent time periods begin sequentially after an end of the first time period;
a time-varying filter coupled to the biosensor; and
a processor coupled to the biosensor and the time-varying filter;
wherein the time-varying filter comprises:
a plurality of low-pass filters coupled in series; and
a plurality of switches, wherein each of the plurality of switches is coupled in parallel with one of the plurality of low-pass filters;
wherein the processor, when executing computer-executable instructions, controls the time-varying filter to apply a level of filtering to the signal during the first time period and each subsequent time period of the plurality of subsequent time periods, the processor:
opening at least one of the plurality of switches for the first time period to apply a first level of filtering to the signal from at least one of the plurality of low-pass filters during the first time period; and
opening at least an additional one of the plurality of switches for each subsequent time period of the plurality of subsequent time periods such that an increased number of low-pass filters of the plurality of low-pass filters apply a level of filtering to the signal relative to an immediately prior number of low-pass filters of the plurality of low-pass filters applying a level of filtering to the signal during an immediately prior subsequent time period,
wherein for each level of filtering for each subsequent time period, the level of filtering is increased relative to an immediately prior level of filtering corresponding to an immediately prior time period to thereby provide consistently increased levels of filtering of the signal across the plurality of subsequent time periods.

27. The system of claim 26,
wherein the wearable device attaches to a user's skin, and wherein the biosensor comprises:
a working electrode contacting interstitial fluid of a user when the biosensor is implanted under a user's skin, the working electrode generating the signal during the analyte monitoring period,
wherein the signal is a measured current signal.

28. The system of claim 27,
wherein the wearable device further comprises:
a guard ring surrounding the working electrode, the guard ring being coupled to a guard source,
wherein the guard ring reduces interference of stray current on the working electrode.

29. The system of claim 27,
wherein the processor, when executing computer-executable instructions:
controls the time-varying filter to apply a level of filtering to the measured current signal during the first time period and each subsequent time period of the plurality of subsequent time periods to produce a filtered measured current signal during the analyte monitoring period;
calculates analyte concentrations from the filtered measured current signal; and
generates a filtered continuous analyte monitoring signal from the analyte concentrations.

30. The system of claim 29, further comprising:
an external device comprising a transceiver and a display, the external device wirelessly communicating with a transceiver comprised in the wearable device,
wherein the transceiver comprised in the wearable device transmits the filtered continuous analyte monitoring signal to the external device for displaying the filtered continuous analyte monitoring signal on the display.

\* \* \* \* \*